(12) United States Patent
Li et al.

(10) Patent No.: US 10,053,744 B2
(45) Date of Patent: Aug. 21, 2018

(54) YEAST STRAIN WITH HIGH YIELD OF GLUTATHIONE

(71) Applicant: Ningxia RisingMark I.P. Consulting Co., Ltd., Beijing (CN)

(72) Inventors: Ji Li, Beijing (CN); Bingdian Li, Beijing (CN)

(73) Assignee: Ningxia RisingMark Intellectual Property Consulting Co., Ltd., Beijing (CN)

( * ) Notice: Subject to any disclaimer, the term of this patent is extended or adjusted under 35 U.S.C. 154(b) by 0 days.

(21) Appl. No.: 15/390,684

(22) Filed: Dec. 26, 2016

(65) Prior Publication Data

US 2018/0135142 A1     May 17, 2018

(30) Foreign Application Priority Data

Nov. 15, 2016   (CN) .................. 2016 1 10324241

(51) Int. Cl.
| | |
|---|---|
| *C12N 9/16* | (2006.01) |
| *C12R 1/865* | (2006.01) |
| *C12P 13/02* | (2006.01) |
| *C12N 15/63* | (2006.01) |
| *C12N 1/10* | (2006.01) |
| *C12N 1/18* | (2006.01) |

(52) U.S. Cl.
CPC ............. *C12R 1/865* (2013.01); *C12P 13/02* (2013.01); *C12N 1/18* (2013.01); *C12N 9/16* (2013.01)

(58) Field of Classification Search
CPC . A61K 38/063; C12N 1/08; C12Y 108/01007
USPC .................. 435/6.15, 254.21, 255.2, 196
See application file for complete search history.

(56) References Cited

FOREIGN PATENT DOCUMENTS

| | | |
|---|---|---|
| CN | 2003113418 | 10/2003 |
| CN | 200810105972 | 11/2009 |
| CN | 201511003961 | 4/2016 |

*Primary Examiner* — Teckchand Saidha
*Assistant Examiner* — Mohammad Y Meah

(57) ABSTRACT

The present invention discloses a yeast strain with high yield of glutathione, and belongs to the technical field of microorganisms. *Saccharomyces cerevisiae* tlj2016 provided in the present invention has been deposited in China General Microbiological Culture Collection Center of Microbe Preservation Management Committee, with a preservation number of CGMCC No. 12789. The strain can tolerate glucose with tolerance capability reaching 300 g/L, and has tolerance capability against L-cysteine that is far higher than that of the starting strain, contributing to the production of glutathione at conditions of high concentrations of glucose, with a final concentration of GSH produced through fermentation in a 5-L fermentation tank reaching 3308 mg/L.

1 Claim, No Drawings

YEAST STRAIN WITH HIGH YIELD OF GLUTATHIONE

TECHNICAL FIELD

The present invention belongs to the technical field of microorganisms, and particularly relates to a yeast strain with high yield of glutathione.

BACKGROUND ART

Glutathione (GSH) is a biologically active tripeptide compound formed by condensation of L-glutaminic acid, L-cysteine and glycine, and is widely present in animal, plant and microbial cells. GSH has a variety of important physiological functions within organisms, and particularly plays an important role in the maintenance of a suitable oxidation-reduction environment within the organisms, so that it has wide applications in clinical, food and cosmetic industries.

Methods for producing GSH mainly include chemical synthesis methods, enzyme methods, fermentation methods and the like. In the chemical synthesis methods, three precursor amino acids are used as raw materials to carry out chemical synthesis, but it is not easy to separate the resulting active products and thus the product purity is not high, so that the application of these methods is limited. In the enzyme synthesis, three substrate amino acids and GSH within the organisms are used to synthesize related enzymes, and GSH is synthesized by the addition of a small amount of ATP. This method suffers from complex operation and higher cost. In the fermentation methods, low-cost sugars may be used as raw materials, to synthesize GSH through specific microbial metabolism, which is simple in operation, lower in cost, higher in the production rate, and easy to upscale. Therefore, increasing importance is attached to the production of GSH by fermentation methods.

In the microbial world, strains generating GSH mainly concentrate in eukaryotic yeasts and Gram negative bacteria. Wild *Saccharomyces cerevisiae* and *Candida utilis* themselves have relatively high GSH contents, and can continuously maintain GSH synthesis capability, and therefore they have become the most common strains in the industrial production of GSH.

Chinese Invention Patent Application with an Application No. 201511003961.9 titled "*Saccharomyces cerevisiae* with high yield of glutathione and use thereof" discloses *Saccharomyces cerevisiae* with high yield of glutathione and use thereof. This yeast has a high yield of glutathione after fermentation culture, and has a short fermentation period. In that invention, carbon and nitrogen sources, vitamins, and precursor amino acids are sequentially added respectively in a manner of supplement by sequential addition to promote the synthesis of glutathione, so as to increase the glutathione content within yeast cells, and effectively solve the problems of low glutathione synthesis capability of yeasts and low glutathione contents in dry yeasts.

Though wild *Saccharomyces cerevisiae* and *Candida utilis* themselves have higher GSH contents, the yields thereof are only suitable for use in laboratory studies, and cannot satisfy requirements in industrial production. Screening strains with high yields of GSH on specific media through physical or chemical mutagenesis is a main means to improve the yield and performance of strains.

In general, the GSH content in microbial cells is not high, and accounts for only 0.1 to 1% of dry weight of the cells. GSH at a too high content will be easy to impair the oxidation-reduction environment that has been balanced in the cells. GSH is an intracellular product and needs extraction in the practical production process, and a lower content thereof will no doubt greatly increase the production cost. Therefore, how to improve the cell density and intracellular GSH content has become a key issue in the production of GSH through fermentation methods.

Chinese Patent with an Application No. 200810105972.1 titled "a *Saccharomyces cerevisiae* strain, dry yeast rich in reduced glutathione and preparation method thereof" provides a yeast strain (CCTCC M 205130) with a higher content of reduced glutathione and stable performance screened out through an ultraviolet mutagenesis method. The strain of this invention is directly used together with yeast cells without extracting and purifying glutathione so as to obtain the dry yeast rich in reduced glutathione.

Moreover, many functions of GSH are exhibited mainly by a mercapto group in the molecule, and the mercapto group is provided by L-cysteine in the synthesis process of GSH. Typically, the amount of L-cysteine synthesized in the cells themselves is lower, which also becomes a limiting factor in large-scale synthesis of GSH in cells. Therefore, exogenous addition of L-cysteine is more effective for the improvement in the GSH synthesis rate.

Chinese Invention Patent with a Patent No. ZL03113418.1 titled "Method for improving yield of glutathione produced by fermentation with tornla yeast" discloses a method for producing glutathione by fermentation, including: adopting torula yeast as the fermentation strain, and after slant culture and seed culture, adding L-cysteine into the fermentation culture medium, to increase supply of L-cysteine in the fermentation broth, so as to improve the synthesis rate and yield of glutathione.

However, an excess of L-cysteine will influence the cell growth. No method exists in the prior art yet that can cross this barrier.

SUMMARY OF THE INVENTION

In order to solve the above technical problems, the present invention provides a *Saccharomyces cerevisiae* strain obtained by mutagenesis which has higher osmotolerance, can grow at a condition of high-concentration glucose, improves cell density, at the same time can accumulate a substantial amount of GSH within cells, and improves the yield of GSH produced through fermentation.

CGMCC No. 12789 has been deposited in China General Microbiological Culture Collection Center (CGMCC ; Institute of Microbiology, Chinese Academy of Sciences, No. 3, No. 1 Yard, West Beichen Road,Chaoyang District, Beijing City, China, 100101) on Jul. 15, 2016, and its proposed taxonomic name is *Saccharomyces cerevisiae*, culture reference given by depositor is tlj2016. The strain was deposited at CGMCC under the Budapest Treaty and will be made available to the public upon issuance of a patent.

*Saccharomyces cerevisiae* tlj2016 has an optimum growth pH from 6.0 to 6.5, and an optimum growth temperature from 28 to 35° C.

*Saccharomyces cerevisiae* tlj2016 is obtained from a starting strain of *Saccharomyces cerevisiae* obtained by separation from an orchard in Ningxia through the following steps:

Original starting strain→activation in test tubes→mutagenesis with diethyl sulfate (DES)→screening on hypertonic flat plates→screening by mutagenesis with nitrosoguanidine (NTG)→primary screening on hypertonic flat plates→screening in shake flasks→secondary screening by fermentation (GSH production capability)→passage stability test.

The strain tlj2016 obtained from the mutagenesis has both improved glucose tolerance and L-cysteine tolerance. On the one hand, culturing at higher concentration of glucose can improve cell density, and on the other hand the improvement in the L-cysteine tolerance will contribute to synthesis of a substantial amount of GSH in cells, thereby improving the capability of large scale production of GSH by the strain.

Beneficial Effects:

1. *Saccharomyces cerevisiae* provided in the present invention has glucose tolerance reaching 300 g/L, which is beneficial to the production of GSH at a condition of high-concentration glucose;

2. *Saccharomyces cerevisiae* provided in the present invention produces GSH by fermentation in a 5-L fermentation tank at a final concentration reaching 3308 mg/L;

3. *Saccharomyces cerevisiae* provided in the present invention has L-cysteine tolerance far higher than that of the starting strain, can still grow slowly under the action of 5 mmol/L L-cysteine, and can still maintain synthesis of a substantial amount of GSH under the action of 40 mmol/L L-cysteine; and 4. *Saccharomyces cerevisiae* provided in the present invention has salt tolerance reaching 18%, which contributes to the expansion in application fields thereof.

DESCRIPTION OF THE PREFERRED EMBODIMENTS

EXAMPLE 1

Mutagenesis of Strain

1. DES Mutagenesis and Selective Breeding
1) On a super-clean bench, one ring of starting strain 1 on a test tube slant was inoculated into a 250-mL triangular flask charged with 50 mL of a malt wort medium, and cultured at 200 rpm and 30° C. for about 10 h, to allow cells to be in an early-log growth phase.
2) 5 mL of the culture broth above was taken and centrifugated for 10 min at 5000 rpm to collect the cells, and the cells were washed twice with normal saline.
3) The cells were diluted with a pH 7.0 phosphate buffer to $10^7$/mL of a cell suspension.
4) 32 mL of a pH7.0 potassium phosphate buffer, 8 mL of the cell suspension, and 0.4 mL of DES were taken, and intensively mixed in a 150-mL triangular flask into which a rotor was placed in advance, to allow DES to have a final concentration of 1% (v/v).
5) The mixture was reacted in a shaker at 30° C. and 150 rpm for 30 min, and 1 mL of the mixed solution was taken, into which was added 0.5 mL of a 25% $Na_2S_2O_3$ solution to stop the reaction.
6) The resultant was diluted and coated into a malt wort medium plate containing 150 g/L KCl. After cultured at 30° C. for 2 to 3 days, the strain 1 with the maximal colony was picked out.

2. Mutagenesis with Nitrosoguanidine
1) On a super-clean bench, one ring of *Saccharomyces cerevisiae* strain 1 on a test tube slant was taken, inoculated into a 250-mL triangular flask charged with 50 mL of the malt wort medium, and cultured at 200 rpm and 30° C. for about 10 h, to allow cells to be in an early-log growth phase.
2) 5 mL of the culture broth above was taken and centrifugated for 10 min at 5000 rpm to collect the cells, and the cells were washed twice with the normal saline.
3) The cells were diluted with a pH6.0 phosphate buffer to $10^7$/mL of a cell suspension.
4) 10 mL of the cell suspension was transferred into a 100-mL triangular flask, and 10 mg of NTG was added therein, to formulate an NTG solution at a final concentration of 10 mg/mL, and 4 to 5 drops of acetone were added therein to favor the dissolution of NTG
5) Reaction was carried out for 30 min with shaking at 30° C. and 200 rpm, and centrifugated at 5000 rpm for 10 min to collect the cells, and the cells were washed several times with sterile normal saline to stop the reaction.
6) The resultant was diluted appropriately, and 0.2 mL of the cell liquid at the final dilution was taken and coated into a malt wort medium plate containing 200 g/L KCl. After cultured at 30° C. for 2 to 3 days, 20 colonies were picked out.

3. Primary Screening in Shake Flasks
1) On a super-clean bench, one ring each of *Saccharomyces cerevisiae* of the above 20 colonies of *Saccharomyces cerevisiae* was taken respectively, inoculated respectively into a 250-mL triangular flask charged with 50 mL of the malt wort medium, and cultured at 200 rpm and 30° C. for about 12 h, to allow cells to be in a mid-log growth phase.
2) 5 mL of culture liquid was taken, inoculated into a 250-mL triangular flask charged with 50 mL of a hypertonic malt wort medium (at a glucose concentration of 300 g/L), cultured for 3 to 4 days at 200 rpm and 30° C., and detected for changes in glucose concentration and ethanol concentration every day. After completion of the fermentation, glucose and ethanol consumption rates, final residual sugar concentration and ethanol concentration, conversion rates of ethanol by glucose, and heteroacid contents were compared among the 20 strains.
3) 5 strains with higher glucose consumption rates, lower final residual sugar concentrations and higher ethanol concentrations were selected and designated as Y-1, Y-2, Y-3, Y-4, and Y-5.

4. Secondary Screening by Fermentation
The 5 strains Y-1, Y-2, Y-3, Y-4, and Y-5 obtained in Step 3, as well as the starting strain were cultured respectively, at an inoculum size of 10%, for 30 h at 150 rpm and 30° C. in a 250-mL shake flask charged with 30 mL of a liquid culture medium. Fermentation broth was sampled to determine the GSH concentration.

Liquid culture medium (g/L): $(NH_4)_2SO_4$ 6, glucose 35, $K_2HPO_4 \cdot 3H_2O$ 3, $KH_2PO_4$ 0.5, yeast powder 11, $MnSO_4$ 0.1, KCl 0.1, $FeSO_4$ 0.1, $MgSO_4 \cdot 7H_2O$ 0.1.

GSH determination method: fresh yeasts were obtained by centrifuging and washing the fermentation broth, and treated for 3 h with 40% ethanol at 30° C. The mixture was centrifuged and the supernatant was taken to serve as a sample for GSH determination.

GSH determination was carried out employing an alloxan method, with a principle as follows. —SH on GSH is reacted with alloxan, the resultant substance has an absorption peak at 305 nm, and the absorbance of the resultant substance is in linear relationship with glutathione concentration, so that the GSH content can be quantitatively determined using an ultraviolet spectrophotometer.

TABLE 1

GSH detection results

| | Strain | | | | | |
|---|---|---|---|---|---|---|
| | Starting strain | Y-1 | Y-2 | Y-3 | Y-4 | Y-5 |
| GSH concentration (mg/L) | 127.9 | 195.7 | 172.3 | 263.2 | 216.5 | 185.2 |

It can be known from the results in Table 1, the strain Y-3 has the best GSH fermentation capability, and thus Y-3 was determined to be the final strain for use in production and designated as tlj2016.

5. Hereditary Stability Test

The tlj2016 strains were passaged 10 times serially on slants, and detected for the fermentation situation after each passage, using a method of secondary screening in shake flasks. Experiments showed that, after 10 serial passages on the slants, the strain had no evident changes in traits thereof, and each performance index was normal, indicating that the strain has strong hereditary stability.

EXAMPLE 2

Experiment of GSH Production Capability by tlj2016 Through Fermentation at High-Sugar Condition (1) Shake-Flask Culture One ring of the tlj2016 slant strain was taken and inoculated into a 250-mL shake flask charged with 30 mL of the shake-flask medium, and cultured for 30 h at 150 rpm and 30° C. to obtain a seed broth.

Shake-flask culture medium (g/L): $(NH_4)_2SO_4$ 6, glucose 35, $K_2HPO_4 \cdot 3H_2O$ 3, $KH_2PO_4$ 0.5, yeast powder 11, $MnSO_4$ 0.1, KCl 0.1, $FeSO_4$ 0.1, $MgSO_4 \cdot 7H_2O$ 0.1, pH6.0.

(2) Culturing in a 5-L Fermentation Tank

The seed broth was inoculated at an inoculum size of 10% into a fermentation tank charged with 3 L of a fermentation medium, and subjected to fermentation culture at a condition of 30° C., ventilatory capacity of 6 L/min, a tank pressure of 0.03 MPa, 500 rpm, and constant pH6.0. L-cysteine at a final concentration of 25 mmol/L was added therein in one portion after fermentation for 30 h, with a total fermentation time of 50 h.

Fermentation medium (g/L): $(NH_4)_2SO_4$ 10, glucose 100, $K_2HPO_4 \cdot 3H_2O$ 8, $KH_2PO_4$ 0.5, yeast powder 11, $MnSO_4$ 0.1, KCl 0.1, $FeSO_4$ 0.1, $MgSO_4 \cdot 7H_2O$ 0.1, pH6.0.

After completion of the fermentation, the GSH content in the fermentation broth was determined to be 3308 mg/L.

EXAMPLE 3

Experiment of L-Cysteine Tolerance

One ring each of the starting strain and the tlj2016 slant strain was inoculated respectively into a 250-mL shake flask charged with 30 mL of the shake-flask medium, and cultured at 150 rpm and 30° C. After 12 h of culture, L-cysteine at various final concentrations was added into the shake flasks and then cultured for 10 h, and dry weight of cells was determined, with results shown in Tables 2 and 3.

Shake-flask culture medium (g/L): $(NH_4)_2SO_4$ 6, glucose 20, $K_2HPO_4 \cdot 3H_2O$ 3, $KH_2PO_4$ 0.5, yeast powder 11, $MnSO_4$ 0.1, KCl 0.1, $FeSO_4$ 0.1, $MgSO_4 \cdot 7H_2O$ 0.1, pH6.0.

TABLE 2

L-cysteine tolerance of starting strain

| | L-Cysteine concentration, mmol/L | | | | | |
|---|---|---|---|---|---|---|
| | 0 | 5 | 10 | 15 | 20 | 40 |
| Dry weight of starting strain, g/L | 22.6 | 15.7 | 10.2 | 4.3 | 2.2 | 0.8 |
| GSH concentration, mg/L | 35.6 | 46.7 | 43.2 | 40.7 | 37.9 | 25.3 |

TABLE 3

L-cysteine tolerance of tlj2016

| | L-Cysteine concentration, mmol/L | | | | | |
|---|---|---|---|---|---|---|
| | 0 | 5 | 10 | 15 | 20 | 40 |
| Dry weight of tlj2016, g/L | 25.7 | 28.5 | 23.6 | 21.2 | 20.6 | 18.7 |
| GSH concentration, mg/L | 73.2 | 98.3 | 113.5 | 121.7 | 127.5 | 135.8 |

As can be seen from results in Table 2, for the starting strain, when L-cysteine was added into the medium, the cells stopped growth and began with autolysis, leading to decrease in the GSH growth rate with the increase in the L-cysteine concentration; however, at a low concentration of L-cysteine, tlj2016 could still grow slowly, and with the increase in the L-cysteine concentration, dry weight of cells of the tlj2016 strain decreased slowly, but the GSH concentration increased continuously. This result will be beneficial for the promotion of GSH production by the addition of precursor amino acid L-cysteine in the GSH production process.

EXAMPLE 4

Experiment of Salt Tolerance

Strains in 1 mL of the tlj2016 culture broth were inoculated into 10 mL of an YPD liquid culture medium (pH=6.5) containing various concentrations of NaCl (with a content gradient of 0%, 2%, 5%, 10%, 15%, and 18%), and placed at 30° C. and cultured for 24 h respectively. Each treatment was repeated in triplicate. 1 ml each of the sample culture broth was taken and intimately mixed into 9 ml of normal saline to prepare dilution solutions. 0.1 ml of the diluent was taken and coated onto an YPD solid flat plate, and cultured upside-down for 36 h in a biochemical incubator at 30° C. (3 parallel samples were prepared for each dilution). The yeast count on the flat plate was recorded and calculated. It can be known from the results as shown in Table 4 that the strain has a salt tolerance concentration of 18%, indicating that the tlj2016 not only can survive in a conventional environment, but also still has vitality at a high-salt condition, so that it can be applied in glutathione production by sugar consumption in processing processes of high-salt food, such as soy sauce and salted products.

TABLE 4

| | Detecion of salt tolerance (×10⁷ cfu/ml) | | | | | |
| --- | --- | --- | --- | --- | --- | --- |
| | NaCl content | | | | | |
| | 0% | 2% | 5% | 10% | 15% | 18% |
| Starting strain | 5.16 ± 0.42 | 4.38 ± 0.42 | 2.15 ± 0.21 | 0.12 ± 0.11 | 0 | 0 |
| tlj2016 | 5.33 ± 0.28 | 5.10 ± 0.71 | 4.83 ± 0.42 | 3.98 ± 0.33 | 2.57 ± 0.48 | 0.83 ± 0.15 |

The invention claimed is:

1. A strain of *Saccharomyces cerevisiae*, characterized in that, the *Saccharomyces cerevisiae* is specifically *Saccharomyces cerevisiae* tlj2016 with accession number of CGMCC No. 12789.

* * * * *